United States Patent [19]
Brown, Sr.

[11] Patent Number: 5,728,165
[45] Date of Patent: Mar. 17, 1998

[54] ADJUSTABLE POST-OPERATIVE PREPARATORY PROSTHETIC SYSTEM

[75] Inventor: Robert N. Brown, Sr., Ithaca, N.Y.

[73] Assignee: Flo-Tech Orthotic & Prosthetic Systems, Inc., Ithaca, N.Y.

[21] Appl. No.: 620,139

[22] Filed: Mar. 21, 1996

Related U.S. Application Data

[63] Continuation-in-part of Ser. No. 379,217, Jan. 27, 1995, Pat. No. 5,571,209.
[51] Int. Cl.$^6$ .................................................. A61F 2/78
[52] U.S. Cl. .................................................. 623/33; 602/62
[58] Field of Search .................... 623/32, 33, 34, 623/35, 36, 37, 38, 23, 60, 62

[56] References Cited

U.S. PATENT DOCUMENTS

| | | | |
|---|---|---|---|
| 4,842,608 | 6/1989 | Marx et al. | 623/33 |
| 4,872,879 | 10/1989 | Shamp | 623/36 |
| 5,529,575 | 6/1996 | Klotz | 623/33 |

FOREIGN PATENT DOCUMENTS

| | | | |
|---|---|---|---|
| 2512666 | 3/1983 | France. | |
| 2103490 | 2/1983 | United Kingdom | 623/33 |

*Primary Examiner*—John G. Weiss
*Assistant Examiner*—Bruce E. Snow
*Attorney, Agent, or Firm*—Harris Beach & Wilcox, LLP

[57] ABSTRACT

A modular apparatus for post-operative use with a transtibial residuum including post-operative adjustable preparatory socket for a patient that has undergone a transtibial amputation. The socket is formed of a single piece of semi-rigid plastic and includes a cup shaped base, a semi-circular rear shell and a semi-circular front shell that are vertically extended from the base. The rear shell has two opposed circumferential cuffs that surround the wearer's leg above the knee. The front shell extends upwardly to a height just below the cuffs. Wide elastic bands surround the upper and lower sections of the device to press the shells into secure contact against the residual limb. A support strap also surrounds the device in the region of the wearer's patella tendon to help absorb some of the impact in the event of a fall. A supra patellar socket formed of a single piece of semi-rigid plastic for use in placer of the post-operative socket after some healing has occurred. An outer socket adapted to fit over both the post-operative socket and the supra patellar socket. The outer socket has a pylon and prosthetic foot attached thereto for allowing the patient to walk on the prosthetic foot.

19 Claims, 7 Drawing Sheets

ADJUSTABLE POST-OPERATIVE PREPARATORY PROSTHETIC SYSTEM

This application is a continuation in part of U.S. application Ser. No. 08/379,217 filed on Jan. 27, 1995 now U.S. Pat. No. 5,571,209.

BACKGROUND OF THE INVENTION

1. Field of the Invention

This invention relates to a modular apparatus for post-operative early and preparatory ambulation of a transtibial residuum.

2. Discussion of the Related Art

Persons who have lost a lower limb can be fitted immediately after surgery with a prosthetic socket to cover the wound during the early stages of rehabilitation. Such amputees are subject to falling because of their initial inability to cope with one limb or simply because the patient forgot that he or she has lost part of a limb and attempts to place weight on the residual limb. These falls can be, at times, dangerous and damaging to the wound and thus extends the rehabilitation period. Therefore, a post-operative prosthesis is needed which will prevent injury to the residual limb in case the wearer attempts to walk on the limb.

After surgery, there is considerable swelling in and about the wound area. The wound is generally dressed and wrapped with a compressive bandage to reduce the swelling. Most post-operative prosthetic devices, although custom fitted, will not maintain pressure contact with the residual limb as the swelling subsides and thus fail to provide the restraint. More importantly, these custom fitted devices do not provide easy or ready access to the wound area when the wound or the bandage needs attention. A post-operative prosthesis is needed which will provide ready access to the wound area.

Following surgery, the patient will go through a lengthy rehabilitation process with the goal that the patient will be fitted with a permanent prosthesis so that he can walk on the prosthesis. The rehabilitation process involves building strength in the residual limb and allowing the patient to become accustomed to using a prosthesis. A post-operative prosthesis is needed which will facilitate the rehabilitation process.

SUMMARY OF THE INVENTION

The present invention includes two sockets adapted to fit over the residual limb successively and adapted to be used with a third outer socket having a pylon and prosthetic foot for allowing the wearer to walk during the rehabilitation process. A post-operative socket is adapted to be fitted over the residual limb immediately following amputation and a supra patellar socket is adapted to be worn after some healing of the residual limb has occurred. Both of these sockets are adapted to fit inside the outer socket which has the pylon and foot attached thereto to allow the patient to begin walking soon after amputation.

The post-operative socket is integrally molded into a single piece of semi-rigid plastic and includes a cup shaped base, a first semi-circular rear shell and a second semi-circular front shell, both of which extend upwardly from the base to form a semi-rigid sleeve for the residual limb. The top section of the rear shell has circumferential cuffs that are arranged to surround the residual limb above the knee. The front shell extends vertically to a height just below the patella (knee cap). Wide elastic bands surround the upper and lower sections of the sleeve and serve to compress the sleeve inwardly against the limb. An adjustable strap is also secured to the rear shell and is passed around the top part of the front shell at about the level of the wearer's patella tendon. The strap is positioned to impart the shock of impact to the lower part of the knee rather than to the wound area.

Once healing allows for limited weightbearing, the post-operative socket is adapted to be fitted with an outer socket which slides over the post-operative socket. The outer socket is adapted to connect to a pylon and prosthetic foot. The outer socket slides over the post-operative socket so that the patient will be able to begin walking on the prosthetic foot. The outer socket is integrally molded into a single piece of semi-rigid plastic and includes a cup shaped base and a first semi-circular rear shell. The outer socket also has a second semi-circular front shell which preferably has a strap attached at the top for attaching a waist strap to the outer socket. The waist strap ensures that the outer socket does not slip with respect to the post-operative socket. Both the front and rear shells extend upwardly from the base to form a semi-rigid sleeve. The outer socket includes, preferably, two straps for tightening the outer socket around the post-operative socket. The base of the outer socket includes means for fastening the pylon to the base such as bolts. The bolts are attached to a plate inside the base.

After additional healing has occurred and the amputation is healthy and ready for full weightbearing, the patient will no longer need the post-operative preparatory socket. Instead, because the patient is in training for use of a permanent prosthesis, a supra patellar socket is substituted for the post-operative preparatory socket. The supra patellar preparatory socket is designed to be used with the same outer socket that is used for the post-operative socket. The outer socket slides over the end of the end of the supra patellar socket. The supra patellar socket includes a base, a rear semi-circular shell and a front semi-circular shell molded into a single piece. The rear semi-circular shell overlaps the front semi-circular shell, forming a cylinder. The rear semi-circular shell terminates at an outwardly projecting shelf, which fits behind the patient's knee. The shelf is shaped to accommodate the hamstrings behind the patient's knee, having recesses corresponding to the positions of the hamstrings. The front semi-circular shell is adapted to receive the patient's patella. Preferably, a pair of straps allow for adjustment of the circumference of the supra patellar socket. A first narrow strap surrounds the supra patellar socket just below the patella. A wide elastic band surrounds the lower portion of the supra patellar socket. The strap and band can be attached to the socket by any conventional means. Preferably, hook and eye type fasteners are used. Near the base of the supra patellar socket are a pair of slots which allow the front shell to move with respect to the rear shell so that the circumference of the socket can be changed. The slots are configured to allow compression of the soft tissues on either side of the residuum, but prevent compression of the sensitive bony and circulatory areas of the residuum. In the front, the slots end such that they align with the posterior edge of the tibia. In the rear, the slots end such that they align with the hamstrings. This configuration assures that compression of the supra patellar socket will not compress the sensitive bony and circulatory areas.

BRIEF DESCRIPTION OF THE DRAWINGS

For a better understanding of the present invention, reference will be made to the following detailed description of the invention which is to be read in conjunction with the accompanying drawings, wherein.

DESCRIPTION OF THE INVENTION

Referring now to the drawings, there are illustrated modular post-operative sockets including a post-operative preparatory socket generally referenced 10, an outer socket 110 and a supra patellar socket 210. The modular sockets are designed to replace awkward and uncomfortable plaster or fiberglass casts that have heretofore been used to cover the wound area of an amputation site. As will become evident from the disclosure below, these post-operative sockets enhance healing and permit the rehabilitation process to begin early.

The present prosthetic sockets 10 and 210 are made of light-weight semi-rigid plastic, preferably polyethylene, and the socket 110 is made preferably from polypropelene and are molded into three single piece structures that can be easily removed and reapplied to the residual limb of a patient that recently underwent a transtibial amputation. The sockets provide ready access to the amputation site so that both the wound and the bandages surrounding the wound can be attended to when such attention is required. The sockets can be easily adjusted to accommodate elastic wraps or shrinkers that are typically applied to the wound area to reduce swelling.

During the critical period of rehabilitation, the post-operative preparatory socket will resist knee flexion contractures while at the same time maintaining proper knee alignment. As the healing process progresses, the semi-rigid adjustable device also helps shape and prepare the residual limb for a permanent prosthesis. It also allows for controlled and measurable weight bearing thus enabling the patient to gradually build the tolerance needed to support his or her body weight in a permanent prosthesis.

As shown in FIGS. 1 and 10–12, the post-operative preparatory socket 10 includes a cup shaped base 12 at its distal end. A pair of semi-circular shaped elongated shells which are integral with the base, extend upwardly from the base section. These shells include a rear shell 13 and a front shell 15. The rear shell 13 is brought to a higher elevation so that it passes over the wearers knee and covers a portion of the wearer's thigh above the knee. The upper part of the rear shell 13 further includes a pair of opposed cuffs 17 and 18 that are arranged to wrap circumferentially around the thigh.

The front shell 15, in turn, is brought to height so that it passes upwardly beyond the level of the wearer's patella tendon. The front shell 15 substantially fills the region under the cuffs 17 and 18 so that the two shells cooperate to form a semi-rigid outer sleeve 16 that can be easily passed over the residual limb and adjusted to accommodate bandages and the like, as well as maintaining a proper fit as swelling is reduced.

The lower section of the front shell is provided with a pair of edge slots or grooves 20—20 at the point where it joins the base section thereby reducing the joint area between the base and the shell. This reduced section 24 of plastic serves as a hinge that allows the front and rear shells to be compressed inwardly to reduce the overall circumference of the lower section of the socket. By the same token, the two opposed cuffs 17 and 18 located at the top section of the rear shell 13 can be compressed to again reduce the circumference in the upper part of the sleeve 16.

A wide elastic band 30 (FIG. 1) is wrapped around the cuffs 17 and 18 and is secured at both ends to the outer wall of the rear shell 13 by means of Velcro fasteners. Loops or eyes 32 are integral to the band 30 on the back of the band 30 which can be attached to hook pads 33—33 secured by any suitable means to the rear shell 13. As can be seen, the band 30 can be drawn tightly around the cuffs 17 and 18 to compress the top section of the sleeve 16 and thus adjustably tighten the cuffs 17 and 18 about the upper part of the patient's limb.

Figure 1:
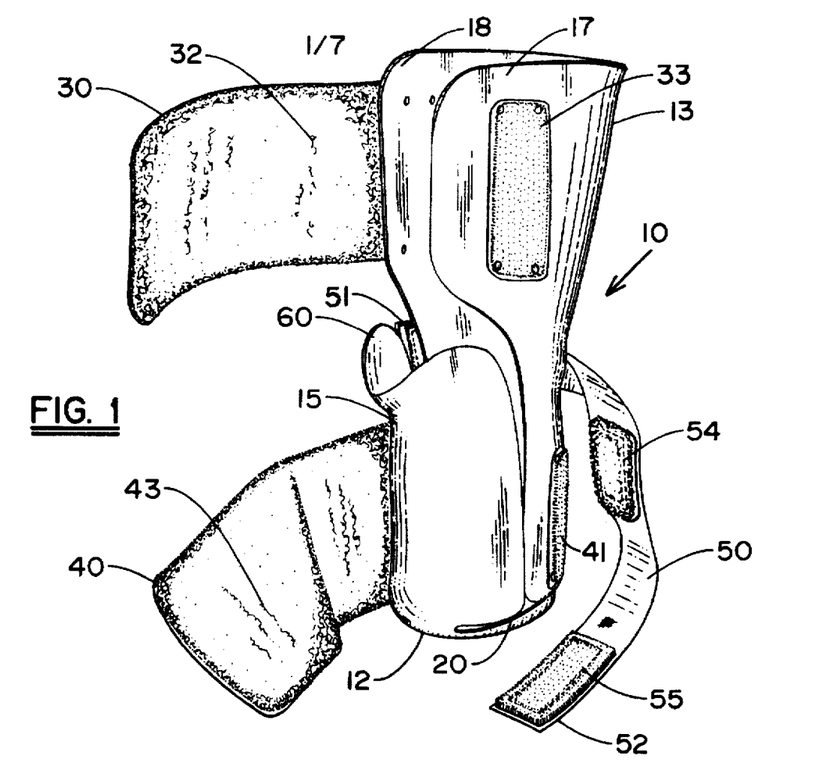
FIG. 1 is a perspective view of the post-operative socket of the present invention.

A second wide elastic band 40 is similarly wrapped about the lower part of the sleeve 16. Here again, a pair of hook pads 41—41 are secured to the rear face of the rear sleeve 16. The band 40 has loops or eyes 43 as an integral part of its back surface. The band 40, in assembly, is attached to one of the pads 41 and is looped around in front of the front shell before being attached to the second pad 41. The band 40 can be selectively tightened around the front shell 15 to draw the front shell 15 inwardly and thus compress the lower section of the front shell 15 about the wearer's limb below the knee.

An adjustable strap 50 is also secured as by rivets to the rear face of the rear shell 15 in the area of the patient's patella tendon. One end of the strap contains a metal loop 51 through which the other free end 52 of the strap 50 can be threaded. A loop pad 54 is sewn into the top face of the strap adjacent to the front shell 15. A cooperating hook pad 55 is similarly sewn into the top face of the strap 50 adjacent to the free end 52 of the strap. In assembly, the free end of the strap is passed around the back and continues around the front of the front shell 15, through the metal loop 51 back onto the strap 50 where the pads are brought together to close the loop.

The upper section of the front shell 15 is provided with an outwardly protruding lip 60 (FIG. 1) that serves to both position the strap in relation to the front shell 15 and locate the strap 50 at about the level of the wearer's patella tendon. This allows the strap 50 to be tightened just below the knee to again draw the front shell 15 inwardly and furnish additional support. The strap, in conjunction with the plastic socket, will absorb a good deal, if not most, of the force of an impact in the event of a fall and transmit this force to the limb in the knee region where it will produce little, if any, harm.

A pair of resilient pads 63 and 64 (FIG. 11) are available to place in the cup of the base thus further cushioning the limb in the event of a fall. The pads 63–64 are preferably available in two inch and one inch thicknesses. The cup 12 is preferably seven inches deep from the lip 60 to the base 12. Pad 63 or 64 or both pads 63 and 64 are placed in the base 12 depending upon the measured length of the amputation stump (residuum).

Figure 3:
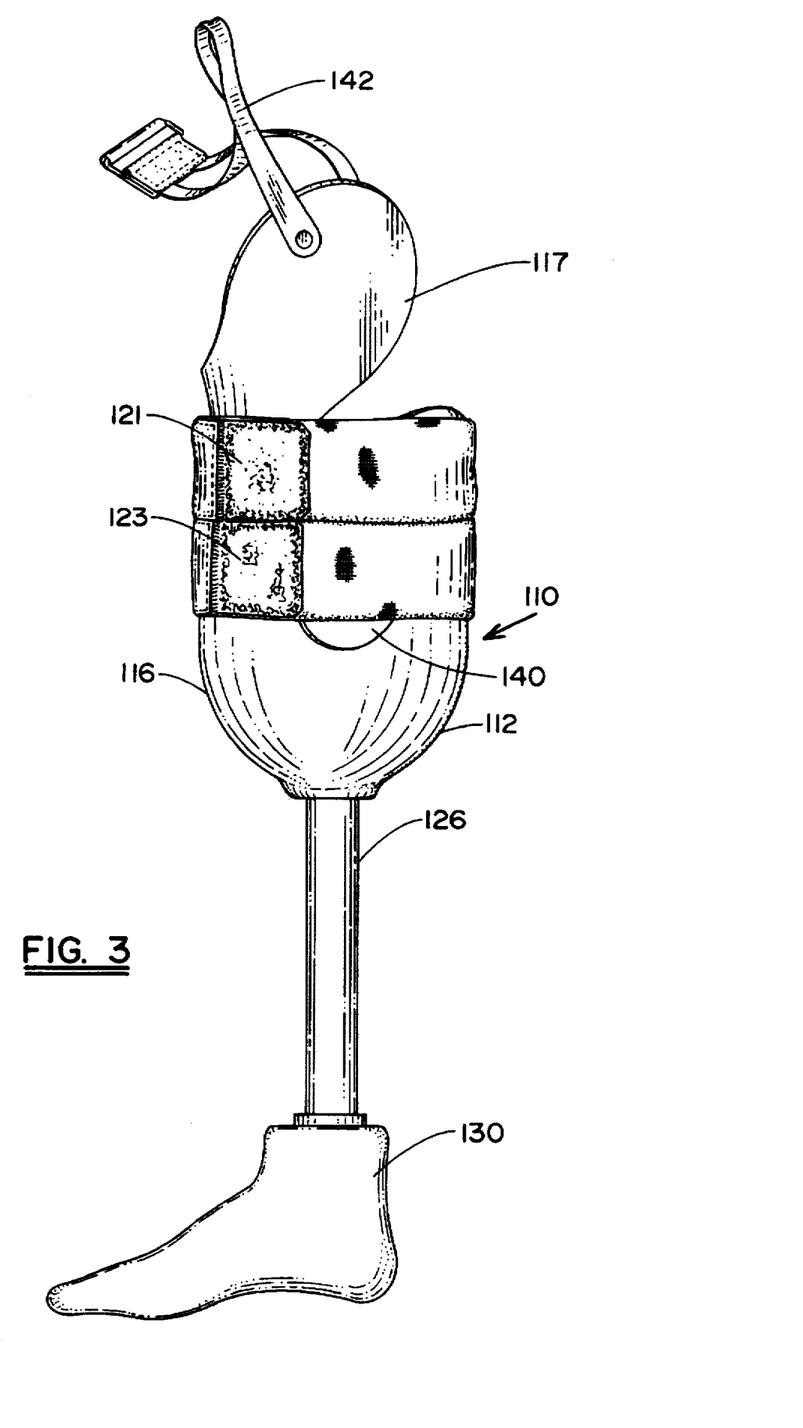
FIG. 3 is a perspective view of the outer socket of the present invention.
Figure 4:
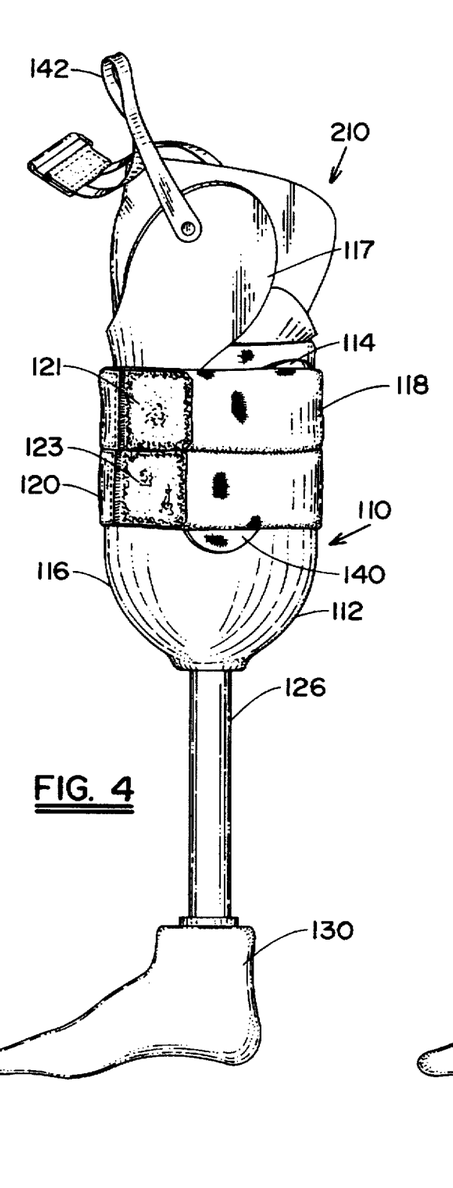
FIG. 4 is a perspective view of the supra patellar socket and the outer socket.
Figure 5:
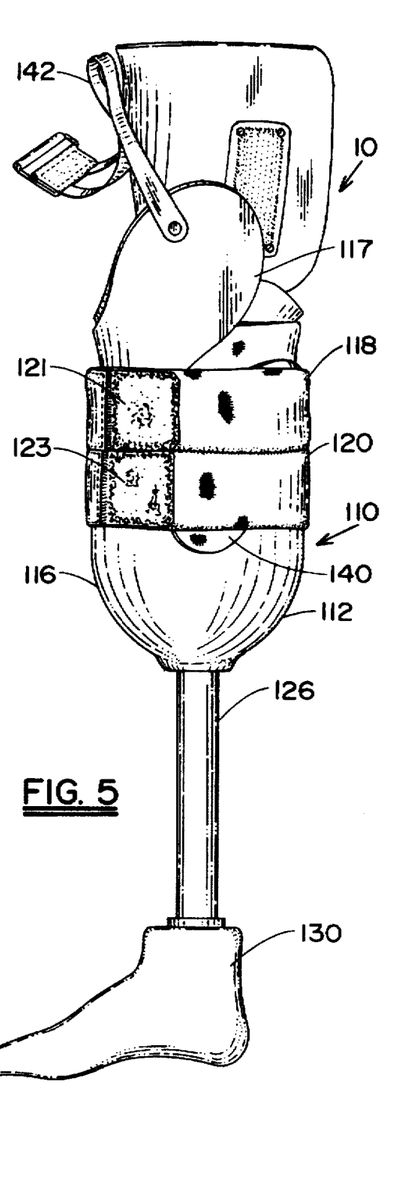
FIG. 5 is a perspective view of the post-operative socket and the outer socket.
Figure 6:
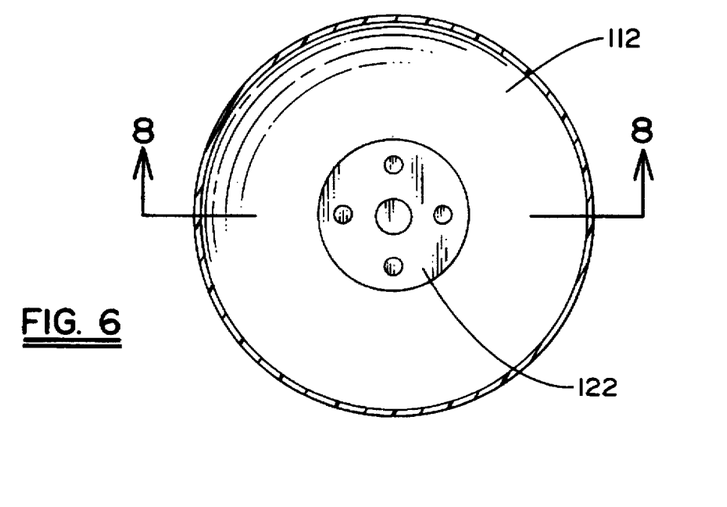
FIG. 6 is a cross-sectional view of the outer socket showing the plate for attaching the pylon and foot.
Figure 7:
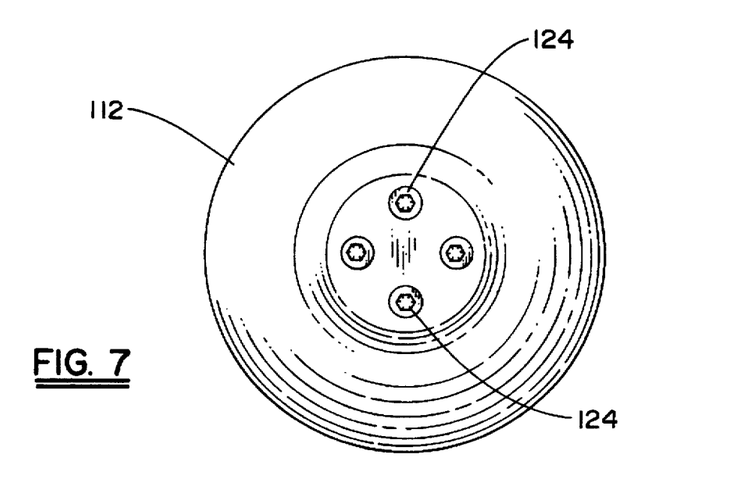
FIG. 7 is a bottom view of the outer socket showing the bolts for attaching the pylon and foot.
Figure 8:
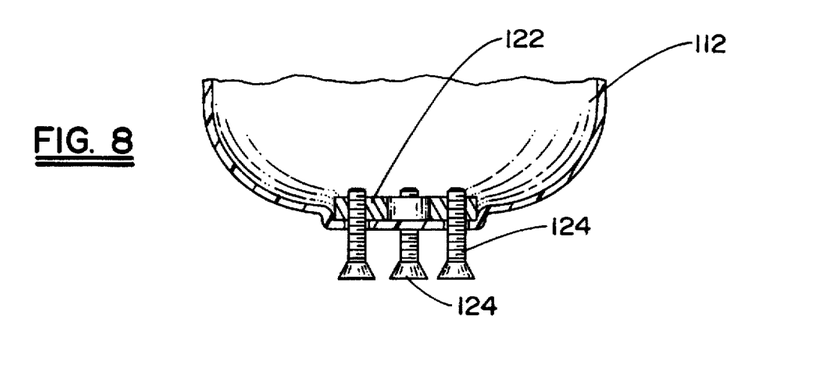
FIG. 8 is a cross-sectional view of the outer socket showing the plate for attaching the pylon and foot.

The post-operative preparatory socket 10 is adapted to be used in connection with the outer socket 110, as seen in FIGS. 3–5. The outer socket 110 is formed as a single piece of semi-rigid plastic and includes a cup-shaped base 112, a front shell 116 and a semi-circular rear shell 114. The front shell 116 has a pair of cuffs or wings 117—117 which extend upward from the front shell 116 to a point above the patient's knee. The cuffs 117—117 extend along each side of the patient's knee and increase the stability of the post-operative socket 10 and outer socket 110 combination. A pair of U-shaped openings 140—140 are formed in both sides of the outer socket 110 so that the diameter of the outer socket 110 can be changed. Two straps 118 and 120 surround the outer socket 110 and can be tightened to ensure a tight fit between the post-operative preparatory socket 10 and the outer socket 110. The straps 118 and 120 are adjusted preferably by hook and eye-type fastening pads 121 and 123 although other fasteners can be used. Optionally, the outer socket 110 includes a strap 142 which can be attached to a belt (not shown) around the patient's waist. The strap 142 and belt ensure that the outer socket 110 remains in place and does not slide off of the post-operative preparatory socket 10. A mounting plate 122 is disposed in the bottom of the outer socket 110 (FIG. 6–8). The mounting plate 122 has a plurality of bolts 124 therethrough. The bolts 124 are adapted to hold a pylon 126 in place. The pylon 126 is in the form of a long rod. A prosthetic foot 130 is attached to the bottom of the pylon 126 such that the patient can walk on the prosthetic foot 130.

Figure 2:
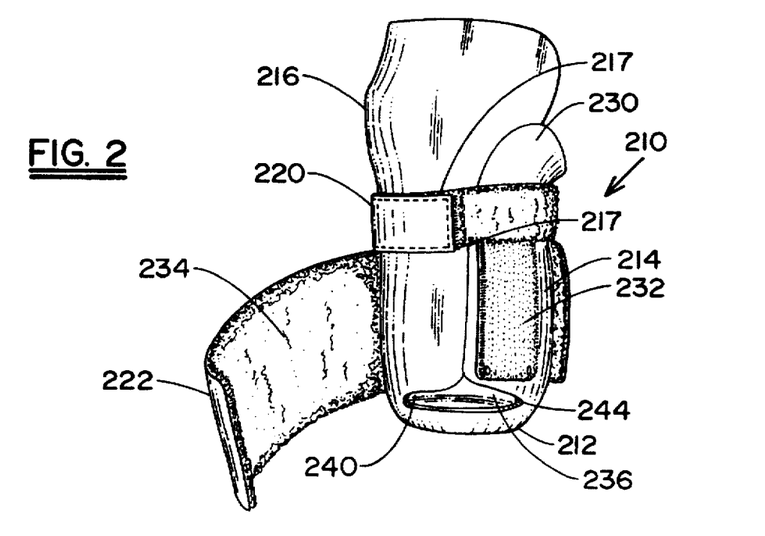
FIG. 2 is a perspective view of the supra patellar socket of the present invention.

After additional healing has occurred and the amputation is ready for full weight bearing, the patient will no longer need the post-operative preparatory socket 10. Instead, a supra patellar socket 210 is indicated (FIG. 2). The supra patellar socket 210 is constructed from one piece of semi-rigid plastic and includes a base 212, rear shell 214 and from shell 216. The front shell 216 extends to a point just above the wearer's knee. The rear shell 214 ends below the wearer's knee and has an outwardly curved shelf 230 which is shaped to accommodate the hamstring tendons behind the knee. The supra patellar socket 210 thus allows the wearer to bend his knee.

The front shell 216 is designed to fit inside of the rear shell 214 so that the diameter of the supra patellar socket 210 can be changed. A strap 220 surrounds the supra patellar socket 210 which can be tightened to change the diameter of the supra patellar socket 210. The strap 220 is adjustable by any conventional means such as hook and eye fastening pads 217, buckle-type fasteners (not shown) or other suitable fastening means. A wide elastic band 222 also surrounds the supra patellar socket 210 to change the diameter of the supra patellar socket 210. The wide elastic band 222 is also adjustable by hook and eye-type fasteners 232 and 234.

Figure 9:
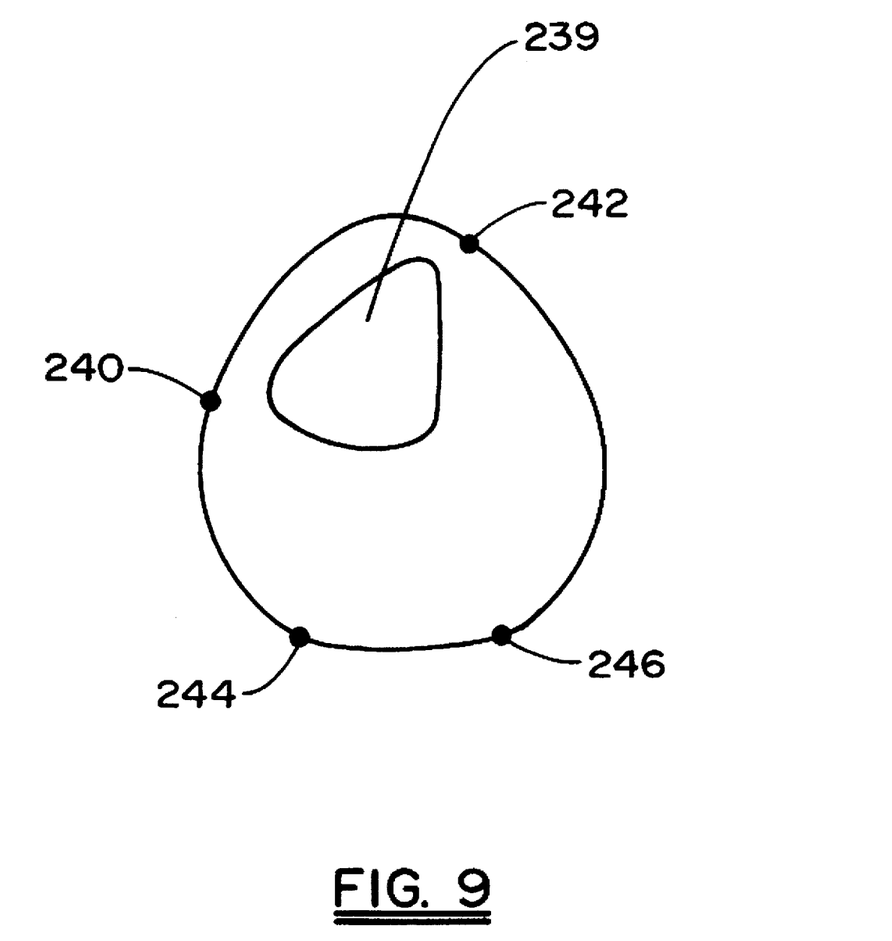
FIG. 9 is a diagrammatic representation of the location of the slots in the supra patellar socket in relation to the patient's tibia.
Figure 10:
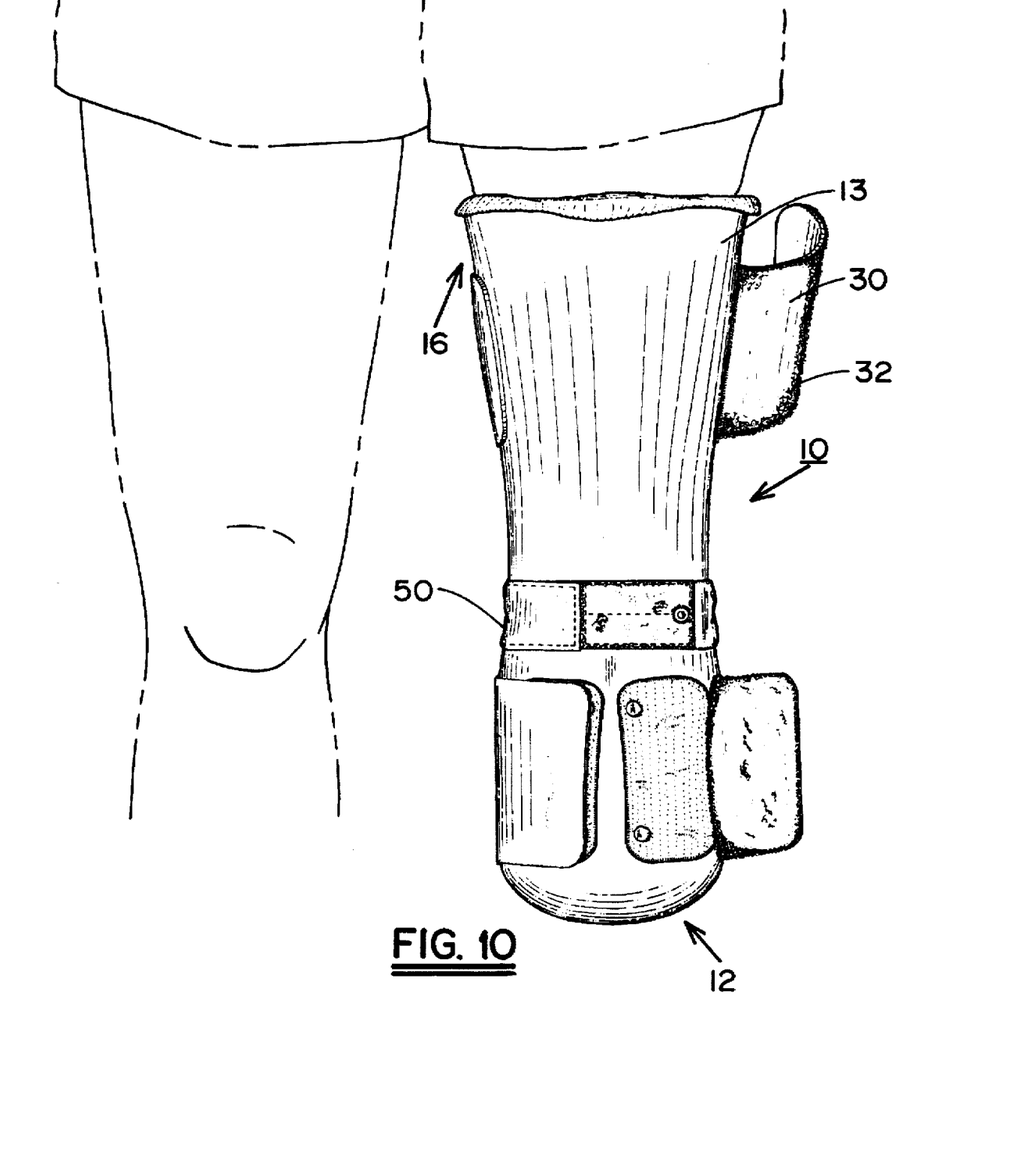
FIG. 10 is a front view showing the post operative socket of the present invention being worn on the residual limb of an amputee who has recently undergone a transtibial amputation.
Figures 11, 12:
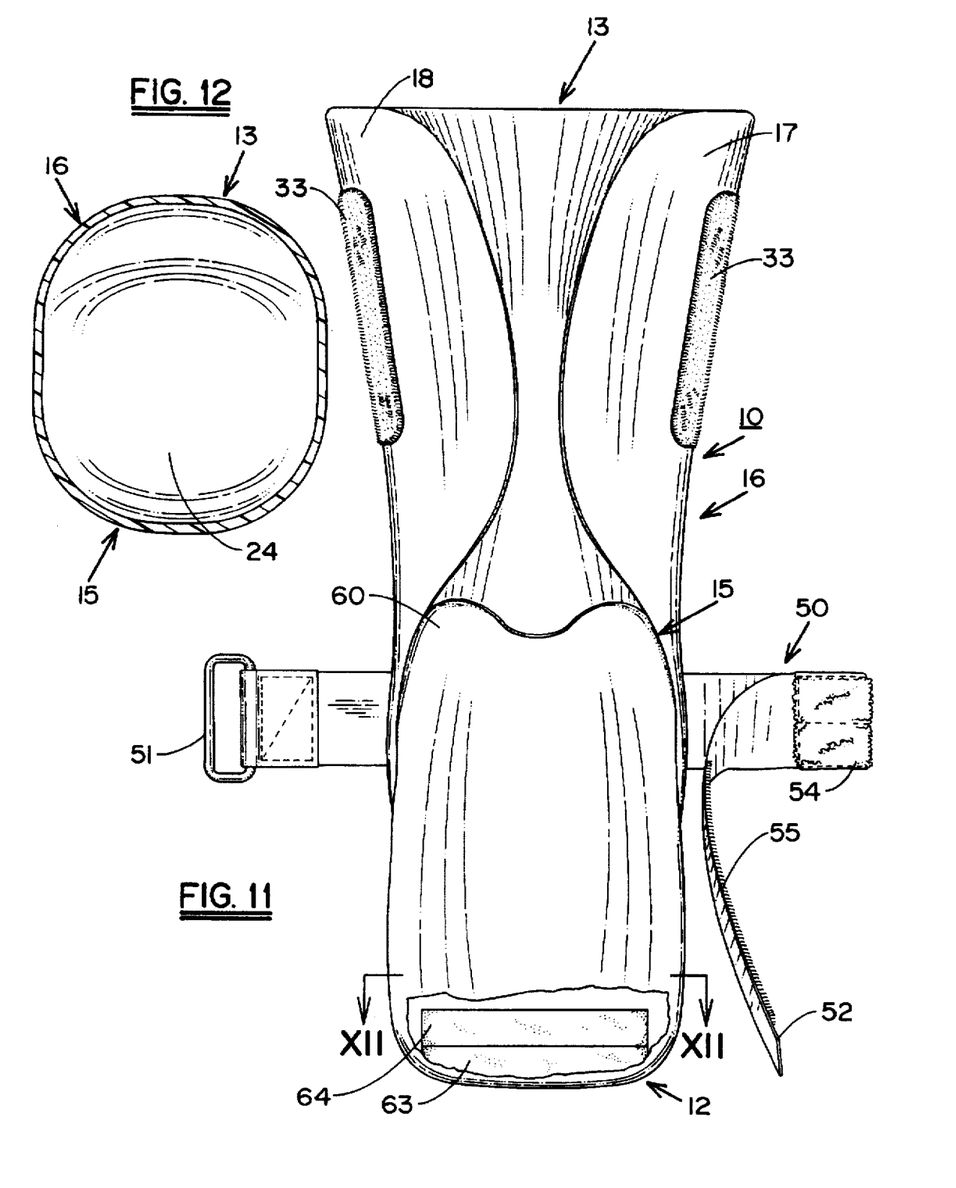
FIG. 11 is a front view of the prosthesis device shown in FIG. 10.
FIG. 12 is a sectional view taken along lines XII—XII in FIG. 11.

The supra patellar socket 210 and the post-operative preparatory socket 10 have a pair of slots or cut-outs 236—236 and 20—20 on either side of the socket 210 and 10 which allow for compression of the residuum. The slots 236 and 20 are configured to allow compression of the soft tissues on either side of the residuum, but prevent compression of the sensitive bony and circulatory areas of the residuum. As represented in FIG. 9, in the front, the slots end such that they align with the posterior edge of the tibia 239 at points 240 and 242. In the rear, the slots 236 and 20 end such that they align with the hamstrings, points 244 and 246. This configuration assures that compression of the supra patellar socket 210 and the post-operative preparatory socket 10 will not compress the sensitive bony and circulatory areas.

The supra patellar socket 210 is designed to fit inside the outer socket 110. Thus, the outer socket 110 fits over either the post-operative preparatory socket 10 or the supra patellar socket 210.

While this invention has been explained with reference to the structure disclosed herein, it is not confined to the details set forth and this invention is intended to cover any modifications and changes as may come within the scope of the following claims:

What is claimed is:

1. A modular prosthesis kit for use by a patient having undergone transtibial amputation and having a residual limb extending below the knee, patella and hamstrings, comprising:

a post-operative socket for a residual limb of a wearer after a transtibial amputation having a cup-shaped base, a semi-circular cross section rear shell and a semi-circular front cross section shell forming a sleeve for receiving the residual limb therein, said rear shell adapted to extend above the knee of the wearer to prevent flexion of the knee;

a supra patellar socket for the residual limb during training for a permanent prosthesis having a cup-shaped base, a semi-circular cross section rear shell and a semi-circular cross section front shell forming a sleeve for receiving the residual limb therein, said rear shell adapted to extend to a point below the knee of the wearer to allow flexion of the knee;

an outer socket having a cup shaped base, a semi-circular cross section rear shell and a semi-circular cross section front shell, said outer socket adapted to fit over and attach securely to both of said post-operative socket and said supra patellar socket such that the wearer of said post-operative socket and said supra patellar socket can attach said outer socket successively to said post-operative socket and said supra patellar socket;

a pylon connected to and extending downward from said outer socket; and a prosthetic foot attached to said pylon.

2. The modular prosthesis of claim 1 wherein said outer socket includes an adjustable strap surrounding said outer socket for securely attaching said outer socket to one of said post-operative socket and said supra patellar socket.

3. The modular prosthesis of claim 1 wherein said outer socket includes a pair of adjustable straps surrounding said outer socket for securely attaching said outer socket to one of said post-operative socket and said supra patellar socket.

4. The modular prosthesis of claim 1 that further includes a pair of circumferential slots formed between the base and the front shell of the post-operative socket to permit the front shell to be compressed inwardly.

5. The modular prosthesis claim 1 wherein said supra patellar socket further includes a pair of slots, each slot extending from a point adjacent the posterior edge of the patient's tibia to a point directly below the patient's hamstrings.

6. The modular prosthesis of claim 1 wherein said front shell of said supra patellar socket is adapted to extend vertically to a point above the knee of the wearer.

7. The modular prosthesis of claim 1 wherein said post-operative socket includes an adjustable strap surrounding the front and rear shells such that the strap can be tightened.

8. The modular prosthesis of claim 7 wherein said front shell of said post-operative socket has a top edge that is turned outwardly to form a lip which prevents the strap from moving over the top of said front shell.

9. The modular prosthesis of claim 7 wherein said post-operative socket includes an elastic band adjustably secured around the post-operative socket such that said post-operative socket can be tightened about said residual limb by said elastic band.

10. The modular prosthesis of claim 9 wherein said elastic band is adjustably secured to one of the shells by means of hook and loop pads.

11. The modular prosthesis of claim 1 wherein said supra patellar socket includes an adjustable strap surrounding said supra patellar socket adapted to securely fasten said supra patellar socket to the residual limb of the wearer.

12. The modular prosthesis of claim 11 wherein said supra patellar socket includes an elastic band adapted to be adjustably secured to the supra patellar socket such that the supra patellar socket can be adjustably closed about the residual limb.

13. The modular prosthesis of claim 12 wherein said rear shell of said post-operative socket includes a pair of opposed cuffs that extend circumferentially from the upper part of the rear shell and are adapted to encompass the wearer's limb above the knee.

14. The modular prosthesis of claim 13 wherein said front shell of said post-operative socket extends vertically to a height just below the circumferential cuffs of said rear shell of said post-operative socket.

15. A modular prosthesis kit for use by a patient having undergone transtibial amputation and having a residual limb extending below the knee, patella and hamstrings comprising:

a one-piece post-operative socket formed of a semi-rigid plastic, said post-operative socket having a circular cup-shaped base, a semi-circular cross section elongated rear shell and a semi-circular cross section front shell, both of which are integral with and extend vertically upwardly from said base to form a sleeve for receiving the residual limb therein, said rear shell having a pair of opposed cuffs that extend circumferentially from the upper part thereof and adapted to encompass the wearer's limb above the knee, said front shell extending vertically to a height just below the circumferential cuffs of said rear shell, elastic means for encircling the sleeve and compressing the shells inwardly toward the wearer's limb, and an adjustable strap secured to the rear shell that surrounds the top of the front shell at about the level of the wearer's patella tendon whereby the strap can be tightened about the shells;

a supra patellar socket for the residual limb during training for a permanent prosthesis having a cup-shaped base, a semi-circular cross section rear shell and a semi-circular cross section front shell, said rear shell adapted to extend to a point below the knee of the wearer to allow flexion of the knee;

an outer socket having a cup shaped base, a semi-circular cross section rear shell and a semi-circular cross section front shell, said outer socket adapted to fit over and attach securely both of said post-operative socket and said supra patellar socket such that the wearer of said post-operative socket and said supra patellar socket can attach said outer socket successively to both said post-operative socket and said supra patellar socket, a pylon connected to and extending downward from said outer socket; and a prosthetic foot attached to said pylon.

16. The modular prosthesis of claim 15 that further includes resilient pad means mounted within said base of said post-operative socket.

17. The prosthetic device of claim 16 wherein said resilient pad means includes a bottom pad affixed to the inside surface of said base and a removable top pad seated upon the bottom pad.

18. A modular prosthesis kit for use by a patient having undergone transtibial amputation and having a residual limb extending below the knee, patella and hamstrings comprising:

a one-piece post-operative socket formed of a semi-rigid plastic, said device having a circular cup-shaped base, a semi-circular cross section elongated rear shell and a semi-circular cross section front shell, both of which extend vertically upwardly from said base to form a sleeve for receiving a residual limb therein, said rear shell having a pair of opposed cuffs that extend circumferentially from the upper part of the rear shell adapted to encompass the wearer's limb above the knee, said front shell extending vertically to a height just below the circumferential cuffs of said rear shell, a first elastic band adjustably secured to the upper part of the rear shell above the wearer's knee, and surrounding the opposed cuffs whereby said cuffs can be adjustably closed about the wearer's limb above the knee;

second elastic band adjustably secured to the lower part of the rear shell below the wearer's knee, said second elastic band surrounding the front shell whereby said front shell can be adjustably closed against the back of the wearer's limb below the knee;

an adjustable strap secured to one of the shells that surround the top of the front shell at about the level of the wearer's patella tendon whereby the strap can be tightened about the shells to provide support below the knee;

a supra patellar prosthesis for the residual limb during training for a permanent prosthesis having a cup-shaped base, a semi-circular cross section rear shell and a semi-circular cross section front shell, said rear shell adapted to extend to a point below the knee of the wearer to allow flexion of the knee;

an adjustable strap surrounding the supra patellar socket to securely fasten said supra patellar socket to the residual limb of the wearer;

an elastic band adjustably secured to the supra patellar socket such that the supra patellar socket can be adjustably closed about the residual limb;

an outer socket having a cup shaped base, a semi-circular cross section rear shell and a semi-circular cross section front shell, said outer socket adapted to fit over and attach securely both of said post-operative prosthesis and said supra patellar prosthesis such that the wearer of said post-operative prosthesis and said supra patellar prosthesis can attach said outer socket successively to said post-operative prosthesis and said supra patellar prosthesis;

a pair of adjustable straps surrounding said outer socket for securely attaching said outer socket to one of said post-operative socket; and a pylon connected to and extending downward from said outer socket;

a prosthetic foot attached to said pylon.

19. The modular prosthesis of claim 18 wherein said supra patella socket further includes a pair of slots formed above said base to allow the supra patellar socket to be compressed inwardly, each slot adapted to extend from a point adjacent the posterior edge of the patient's tibia to a point directly below the patient's hamstrings.

* * * * *